(12) United States Patent
Cotton et al.

(10) Patent No.: US 10,571,402 B2
(45) Date of Patent: Feb. 25, 2020

(54) APPARATUS AND METHOD FOR SENSING

(71) Applicant: Nokia Technologies Oy, Espoo (FI)

(72) Inventors: Darryl Cotton, St Ives (GB); Adam Robinson, Cambridge (GB)

(73) Assignee: Nokia Technologies Oy, Espoo (FI)

(*) Notice: Subject to any disclaimer, the term of this patent is extended or adjusted under 35 U.S.C. 154(b) by 85 days.

(21) Appl. No.: 15/563,704

(22) PCT Filed: Mar. 22, 2016

(86) PCT No.: PCT/FI2016/050175
§ 371 (c)(1),
(2) Date: Oct. 2, 2017

(87) PCT Pub. No.: WO2016/162594
PCT Pub. Date: Oct. 13, 2016

(65) Prior Publication Data
US 2018/0073988 A1   Mar. 15, 2018

(30) Foreign Application Priority Data
Apr. 10, 2015 (EP) .................... 15163254

(51) Int. Cl.
*G01N 21/84* (2006.01)
*G01N 21/63* (2006.01)
(Continued)

(52) U.S. Cl.
CPC ......... *G01N 21/78* (2013.01); *G01N 21/8483* (2013.01); *G01N 27/327* (2013.01);
(Continued)

(58) Field of Classification Search
CPC ............ G01N 21/8483; G01N 21/255; G01N 21/6428; G01N 2021/7783;
(Continued)

(56) References Cited

U.S. PATENT DOCUMENTS 7,740,801 B2 * 6/2010 Saini ..................... G01N 21/76
422/52
2003/0106260 A1 6/2003 Airaudi et al.
(Continued)

FOREIGN PATENT DOCUMENTS

CN   101261269 A   9/2008
EP   1582598 B1   1/2008
(Continued)

OTHER PUBLICATIONS

Wong et al., "Lateral Flow Immunoassay" Springer, 2009, 223 pages.
(Continued)

*Primary Examiner* — Jennifer Wecker
(74) *Attorney, Agent, or Firm* — Harrington & Smith

(57) ABSTRACT

An apparatus and method, the apparatus comprising: an information electrode; a ground electrode; a photo-resistive element configured to enable the information electrode to be connected to the ground electrode; and wherein the apparatus is configured to enable a sensor element to be positioned overlaying the photo-resistive element such that a change in optical properties of the sensor element controls the connection between the ground and information electrodes.

15 Claims, 9 Drawing Sheets

(51) Int. Cl.
   *G01N 21/75*     (2006.01)
   *G01N 27/403*    (2006.01)
   *G01N 27/327*    (2006.01)
   *G01R 31/28*     (2006.01)
   *G01N 21/78*     (2006.01)
   G01N 21/25       (2006.01)
   G01N 27/414      (2006.01)
   B01L 3/00        (2006.01)
   G01N 21/77       (2006.01)

(52) U.S. Cl.
   CPC ....... *G01N 27/403* (2013.01); *G01R 31/2829* (2013.01); *B01L 3/502715* (2013.01); *B01L 2300/0645* (2013.01); *B01L 2300/0816* (2013.01); *G01N 21/255* (2013.01); *G01N 27/3272* (2013.01); *G01N 27/4145* (2013.01); *G01N 2021/7783* (2013.01); *G01N 2021/7786* (2013.01)

(58) Field of Classification Search
   CPC ... G01N 2021/7786; G01N 2021/8488; G01N 21/645; G01N 21/7703; G01N 21/78; G01N 2201/08; G01N 2201/12707; G01N 2201/12723; G01N 2333/96463; G01N 27/327; G01N 27/3272; G01N 27/3273; G01N 27/403; G01N 27/4145; G01N 27/4146; G01N 27/4166; G01N 33/48707; G01N 33/48771; G01N 33/4905; G01N 33/5438; G01N 33/86; B01L 2300/0645; B01L 2300/0809; B01L 2300/0816; B01L 2300/0877; B01L 2400/0487; B01L 2400/0672; B01L 2400/0688; B01L 3/502715; B01L 3/50273; B01L 3/502738; B01L 3/502746; G01R 31/2829; G02B 6/4204; G02B 6/4224; G02B 6/4236; G02B 6/4243; G02B 6/4244; G02B 6/426; G02B 6/4265; G02B 6/4266; G02B 6/4286

See application file for complete search history.

(56) References Cited

U.S. PATENT DOCUMENTS

2008/0069491 A1*  3/2008  Kissa ............... G02F 1/0123
                                                      385/2
   2012/0187956 A1   7/2012  Uzelac et al.
   2012/0283538 A1* 11/2012  Rose .................. A61B 5/14532
                                                      600/347
   2013/0038209 A1*  2/2013  Akasaka ............ H01L 31/0203
                                                      315/77
   2013/0146478 A1*  6/2013  Iyengar ............. G01N 21/7703
                                                      205/775
   2013/0149775 A1   6/2013  Williams et al.
   2014/0170757 A1   6/2014  Tsai et al.
   2014/0327645 A1* 11/2014  Matthews ............... G06F 3/044
                                                      345/174
   2016/0091511 A1*  3/2016  Di Tullio ........... G01N 33/4905
                                                      435/13

FOREIGN PATENT DOCUMENTS

EP     1918708          5/2008
   EP     2153211  A1      2/2010
   EP     2417449  A2      2/2012
   EP     2791672  A1     10/2014
   EP     2980569  A1      2/2016
   GB     2431231          4/2007
   WO     9417556          8/1994
   WO     2008/134811 A1  11/2008
   WO     2010/118185 A2  10/2010
   WO     2013/090394 A1   6/2013
   WO     2014/181033 A1  11/2014

OTHER PUBLICATIONS

"Touchcode", T-ink, Retrieved on Sep. 22, 2017, Webpage available at :http://www.t-ink.com/products/touchcode/.
   "QuickQuant™ Mouse IgG Quantification Kit, 30 tests", BioAssay Works, Retrieved on Sep. 22, 2017, Webpage available at :https://bioassayworks.com/product/quickquant-mouse-igg-quantification-kit-30-tests/.
   GB Non Provisional Application No. 1312879.8, "Apparatuses, Methods and Computer Programs for Expanding the Use of Touch-Sensitive Input Apparatus", filed on Jul. 18, 2013, 29 pages.
   "Reading a Lateral Flow Assay (pregnancy Test) Electronically", Arduino, Retrieved on Sep. 22, 2017, Webpage available at :http://forum.arduino.cc/index.php?PHPSESSID=k96geian5526i1ribbchv8gqk1&topic=207485.msg1525665#msg1525665.
   Extended European Search Report received for corresponding European Patent Application No. 15163254.4, dated Sep. 21, 2015, 7 pages.
   International Search Report and Written Opinion received for corresponding Patent Cooperation Treaty Application No. PCT/FI2016/050175, dated Jun. 6, 2016, 13 pages.
   Office action received for corresponding Vietnam Patent Application No. 1-2017-04401, dated Dec. 5, 2017, 1 pages of office action and 1 pages of office action translation available.

* cited by examiner

APPARATUS AND METHOD FOR SENSING

RELATED APPLICATION

This application was originally filed as PCT Application No. PCT/FI2016/050175 filed Mar. 22, 2016 which claims priority benefit from EP Patent Application No. 15163254.4 filed Apr. 10, 2015.

TECHNOLOGICAL FIELD

Examples of the disclosure relate to an apparatus and method for sensing. In particular they relate to an apparatus and method for sensing wherein the sensing apparatus can be read by a capacitive touch screen.

BACKGROUND

Sensor elements which produce a visible change in the presence of an analyte are known. For example materials which change colour when exposed to a particular analyte may be used to determine the presence of the analyte.

Typically such sensor elements are read manually by a user looking at the sensor element. It would be useful to enable such sensor elements to be read electronically.

BRIEF SUMMARY

According to various, but not necessarily all, examples of the disclosure, there may be provided an apparatus comprising: an information electrode; a ground electrode; a photo-resistive element configured to enable the information electrode to be connected to the ground electrode; and wherein the apparatus is configured to enable a sensor element to be positioned overlaying the photo-resistive element such that a change in optical properties of the sensor element controls the connection between the ground and information electrodes.

In some examples the photo-resistive element may be positioned between the information electrode and the ground electrode.

In some examples the photo-restive element may form part of the information electrode.

In some examples the apparatus may be configured to be placed on a capacitive touch screen to enable a capacitive touch screen and light source to illuminate the sensor element and detect whether or not the information electrode is connected to the ground electrode.

In some examples the apparatus may comprise a polymer coating.

In some examples the apparatus may comprise a plurality of information electrodes.

In some examples the apparatus may comprise a plurality of ground electrodes.

In some examples the apparatus may comprise at least one reference electrode.

In some examples the sensor element may be integrated into the apparatus.

In some examples the sensor element may comprise a material which is arranged to change optical properties in response to an analyte.

In some examples the sensor element may be provided on an at least partially transparent test strip.

In some examples the apparatus may comprise a calibration strip. The calibration strip enables the quantity of the analyte detected by the sensor element to be determined.

In some examples there may be provided a test device comprising an apparatus as described above.

According to various, but not necessarily all, examples of the disclosure, there may be provided a method comprising: providing an information electrode; providing a ground electrode; providing a photo-resistive element configured to enable the information electrode to be connected to the ground electrode; and wherein the photo-resistive element is configured to enable a sensor element to be positioned overlaying the photo-resistive element such that a change in optical properties of the sensor element controls the connection between the ground and information electrodes.

In some examples the method may further comprise positioning the photo-resistive element between the information electrode and the ground electrode.

In some examples the method may further comprise forming part of the information electrode from the photo-resistive element.

In some examples the method may further comprise configuring the sensor element to be placed on a capacitive touch screen to enable a capacitive touch screen and light source to illuminate the sensor element and detect whether or not the information electrode is connected to the at least one ground electrode.

In some examples the method may further comprise providing a polymer coating.

In some examples the method may further comprise providing a plurality of information electrodes.

In some examples the method may further comprise providing a plurality of ground electrodes.

In some examples the method may further comprise providing at least one reference electrode.

In some examples the method may further comprise integrating the sensor element into the apparatus.

In some examples the sensor element may comprise a material which is arranged to change optical properties in response to an analyte.

In some examples the method may further comprise providing the sensor element on an at least partially transparent test strip.

In some examples the method may further comprise providing a calibration strip. The calibration strip may enable the quantity of the analyte detected by the sensor element to be determined.

According to various, but not necessarily all, examples of the disclosure there may be provided examples as claimed in the appended claims.

BRIEF DESCRIPTION

For a better understanding of various examples that are useful for understanding the detailed description, reference will now be made by way of example only to the accompanying drawings in which.

DETAILED DESCRIPTION

Figure 1:
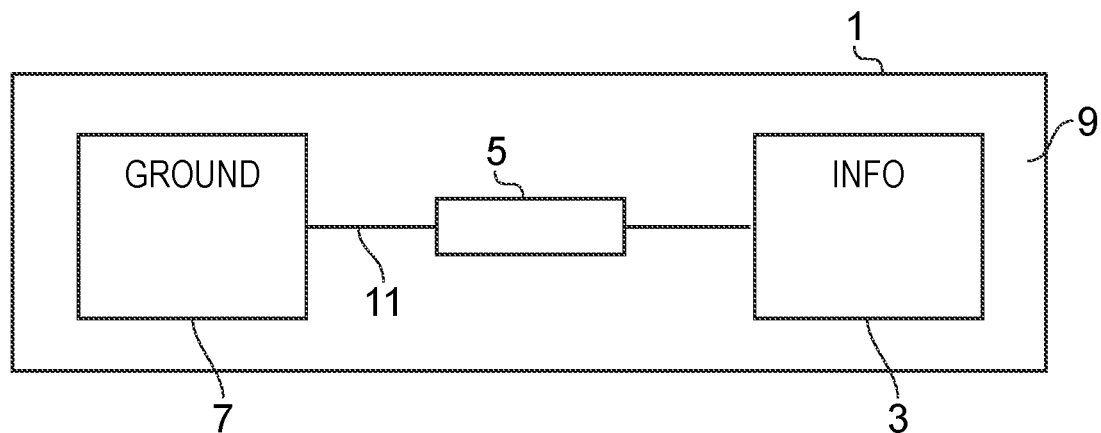
FIG. 1 illustrates an example apparatus.

The Figures illustrate an apparatus 1 comprising: an information electrode 3; a ground electrode 7; a photo-resistive element 5 configured to enable the information electrode 3 to be connected to the ground electrode 7; and wherein the apparatus 1 is configured to enable a sensor element 41 to be positioned overlaying the photo-resistive element 5 such that a change in optical properties of the sensor element 41 controls the connection between the ground and information electrodes 7, 3.

The apparatus 1 may be for sensing. The apparatus 1 may be used to sense the presence of an analyte in a sample or environment. The analyte may cause a change in the optical properties of the sensor element 41. A capacitive touch screen may be used to provide backlighting for measuring the optical properties of the sensor element 41. The capacitive touch screen may also be used to detect whether or not the information electrode 3 is connected to the ground electrode 7.

FIG. 1 schematically illustrates an example apparatus 1. The apparatus 1 comprises an information electrode 3, a ground electrode 7 and a photo-resistive element 5. The electrodes 3, 7 and the photo-resistive element 5 are provided on a substrate 9.

The substrate 9 may be a flat or a substantially flat substrate 9. The electrodes 3, 7 and the photo-resistive element 5 may be printed on the substrate 9. As the substrate 9 is flat or substantially flat this enables the apparatus 1 to be placed over the surface of a capacitive touch screen so that the capacitive touch screen can detect the electrodes 3, 7 and read a sensor element 41.

The substrate 9 may also enable the apparatus 1 to be easily attached to goods or other objects. It is to be appreciated that in other examples the apparatus 1 may have a different shape, for example, the apparatus 1 may be flexible which may enable it to be deformed by a user.

The substrate 9 may be formed from an opaque material. The substrate 9 may be opaque so that when the apparatus 1 is provided on a capacitive touch screen the ambient light does not activate the photo-resistive elements 5.

The information electrode 3 may comprise a portion of conductive material. The portion of conductive material may be sized so that the conductive region can be detected by a capacitive touch screen. The ground electrode 7 may also comprise a portion of conductive material. A conductive trace 11 may be provided between the information electrode 3 and the ground electrode 7. The conductive trace 11 may provide a path for direct current between the ground electrode 7 and the information electrode 3.

In examples of the disclosure a photo-resistive element 5 may be provided between the information electrode 3 and the ground electrode 7. The photo-resistive element 5 may be configured to enable the information electrode 3 to be connected to, and disconnected from, the ground electrode 7. In the example of FIG. 1 the photo-resistive element 5 is provided within the conductive trace 11. In other examples the photo-resistive element 5 may form part of the information electrode 3.

The photo-resistive element 5 may comprise any means which may have a resistance which is dependent on the amount of incident light. The photo-resistive element 5 may comprise a light dependent resistor, a phototransistor such as a GFET (graphene field effect transistor), a functionalized GFET with quantum dots or other functionalization, a photo diode, a photoactive junction, a pyroelectric element or any other suitable means which may be configured to undergo a change in resistivity in response to incident light.

In some examples the photo-resistive element 5 may be configured to be triggered by a specific wavelength or range of wavelengths of light. For instance the photo-resistive element 5 may be configured to be triggered in by red, green or blue light.

The photo-resistive element 5 may be configured to become more conductive when it is exposed to incident light. When there is no incident light on the photo-resistive element 5 the photo-resistive element 5 may have a high resistance which may effectively disconnect the information electrode 3 from the ground electrode 7. This prevents charge transfer between the ground electrode 7 and the information electrode 3. When there is incident light on the photo-resistive element 5 the photo-resistive element 5 may have a low resistance which may enable the information electrode 3 to be connected to the ground electrode 7. This provides a path for direct current between the ground electrode 7 and the information electrode 3 and allows for charge transfer between the ground electrode 7 and the information electrode 3.

When the apparatus 1 is positioned over a capacitive touch screen the capacitive touch screen may be able to detect the information electrode 3 if it is connected to the ground electrode 7. The capacitive touch screen might not be able to detect the information electrode 3 if it is not connected to the ground electrode 7. The information electrode 3 may be connected to the ground electrode 7 when charge can flow between the two electrodes 3, 7. The information electrodes may be disconnected from the ground electrode 7 when charge is prevented from flowing between the electrodes 3, 7. The photo-resistive element 5 may control whether or not the information electrode 3 is connected to the ground electrode 7. Therefore, whether or not the capacitive touch screen can detect the information electrode 3 depends on the whether or not the photo-resistive element 5 has connected or disconnected the information electrode 3 and the ground electrode 7. This will depend on the amount of light incident on the photo-resistive element 5.

The apparatus 1 may be configured to enable a sensor element 41 to be positioned overlaying the photo-resistive element 5. The sensor element 41 may comprise any material which has optical properties which change in response to an analyte. The optical property could be the colour of the material, the transparency of the material, the fluorescence of the material or any other suitable property.

If a sensor element 41 is provided overlaying the photo-resistive element 5 then the amount of light which is incident on the photo-resistive element 5 will be determined by the optical properties of the sensor element 41. Therefore the optical properties of the sensor element 41 control the connection between the information electrode 3 and the ground electrode 7. This enables a capacitive touch screen to be used to read the results from a sensor element 41.

Figure 2:
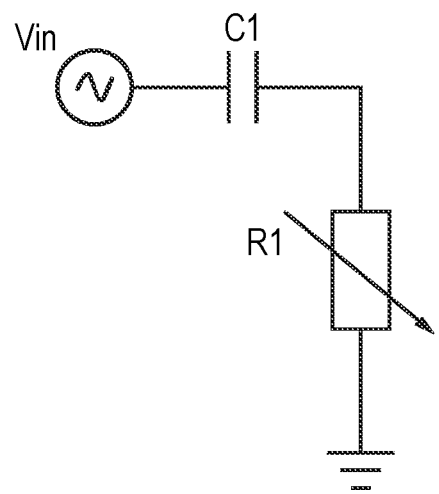
FIG. 2 illustrates an equivalent circuit of the example apparatus.

FIG. 2 illustrates an equivalent circuit of the example apparatus 1 of FIG. 1. The capacitor C1 is the capacitance between the information electrode 3 and a capacitive touch screen. The resistor R1 is a photo-resistive element 5 as described above.

The charge transfer for the circuit can be calculated using the equation:

$$dQ = \frac{V_{in}R}{R^2 + \left(\frac{1}{(2\pi f C_{in})^2}\right)}$$

A mutually capacitive touch screen may be arranged to measure the change in charge coupled between a transmitter electrode and a receiver electrode. When a charge reservoir, such as a user's finger, is placed close to the capacitive touch screen charge is removed from the receiver electrode. When the charge removed from the receiver electrode exceeds a threshold then a touch is registered.

The time constant T of the capacitor C1 is the time it takes to charge the capacitor to approximately two thirds of its maximum when a constant voltage if applied. The time constant is given by

T=RC

Therefore if the resistance R of the photo-resistive element is increased then this will increase the time constant of the capacitor and slow the rate of charge transfer onto the capacitor plate. If the resistance R is high enough then insufficient charge will be transferred onto the capacitor plate for the capacitive touch screen to register an input.

Figure 3:
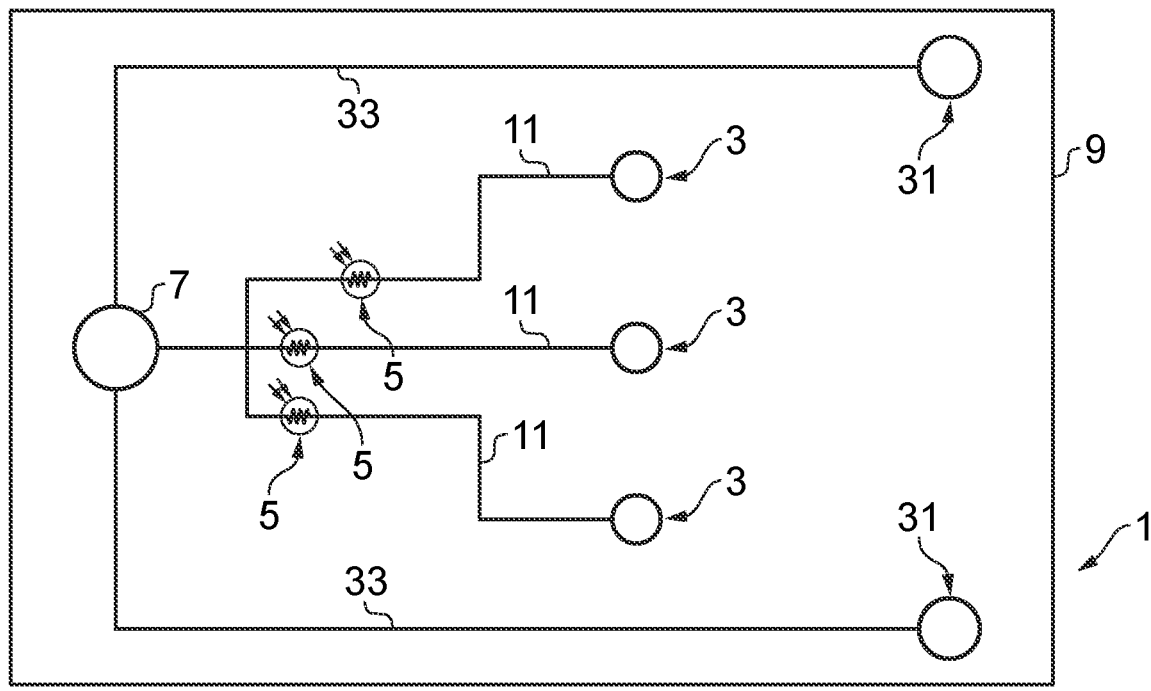
FIG. 3 illustrates an example apparatus comprising a plurality of information electrodes.

FIG. 3 schematically illustrates an example apparatus 1 comprising a plurality of information electrodes 3 and a plurality of photo-resistive elements 5. The apparatus 1 also comprises a ground electrode 7 and a plurality of reference electrodes 31. The electrodes 3, 7, 31 are provided on a substrate 9. The substrate 9 may be as described above.

In the example of FIG. 3 the apparatus 1 comprises three information electrodes 3. Each of the information electrodes 3 may have identical size and shape. Each of the information electrodes 3 are connected to a ground electrode 7 by a conductive trace 11 and a photo-resistive element 5. Each information electrode 3 may be configured to be independently connected to the ground electrode 7. This enables a touch screen to detect each information electrode 3 independently of the other information electrodes 3. Different information electrodes 3 may enable different sensor elements 41 to be read by a capacitive touch screen.

In the example of FIG. 3 three information electrodes 3 and three photo-resistive elements 5 are provided. The number of photo-resistive elements 5 is the same as the number of information electrodes 3. It is to be appreciated that any number of information electrodes 3 and photo-resistive elements 5 may be provided in other examples of the disclosure.

In the apparatus 1 of FIG. 3 one ground electrode 7 is provided and all of the information electrodes 3 are configured to be connected to the same ground electrode 7. In other examples a plurality of ground electrodes 7 may be provided and different information electrodes 3 may be connected to different ground electrodes 7.

The reference electrodes 31 may provide means for enabling a capacitive touch screen 7 to determine the positions of the photo-resistive elements 5 and/or information electrodes 3.

The reference electrodes 31 may comprise portions of conductive material. The portions of conductive material may be sized so that the conductive region can be detected by a capacitive touch screen. The reference electrodes 31 are connected to the ground electrode 7 by a conductive wire or trace 33. The conductive wire or trace 33 may provide a direct current path between the reference electrodes 31 and the ground electrode 7.

In the example of FIG. 3 the reference electrodes 31 are permanently connected to the ground electrode 7. There are no switching elements or sensor elements provided between the reference electrodes 31 and the ground electrode 7. This enables the capacitive touch screen to detect the positions of the reference electrodes 31 regardless of the brightness of the display or the status of a sensor element 41.

In the examples of FIG. 3 the reference electrodes 31 are provided in corners of the apparatus 1. It is to be appreciated that the reference electrodes 31 may be provided in other positions in other examples of the disclosure.

In the examples of FIG. 3 two reference electrodes 31 and a ground electrode 7 are provided. This enables the plane of the surface of the substrate 9 to be identified. It is to be appreciated that other numbers and/or arrangements of reference electrodes 31 may be used in other examples of the disclosure.

In the examples of FIG. 3 the apparatus 1 also comprises a plurality of information electrodes 3. In the example of FIG. 3 three information electrodes 3 are provided.

Figure 4:
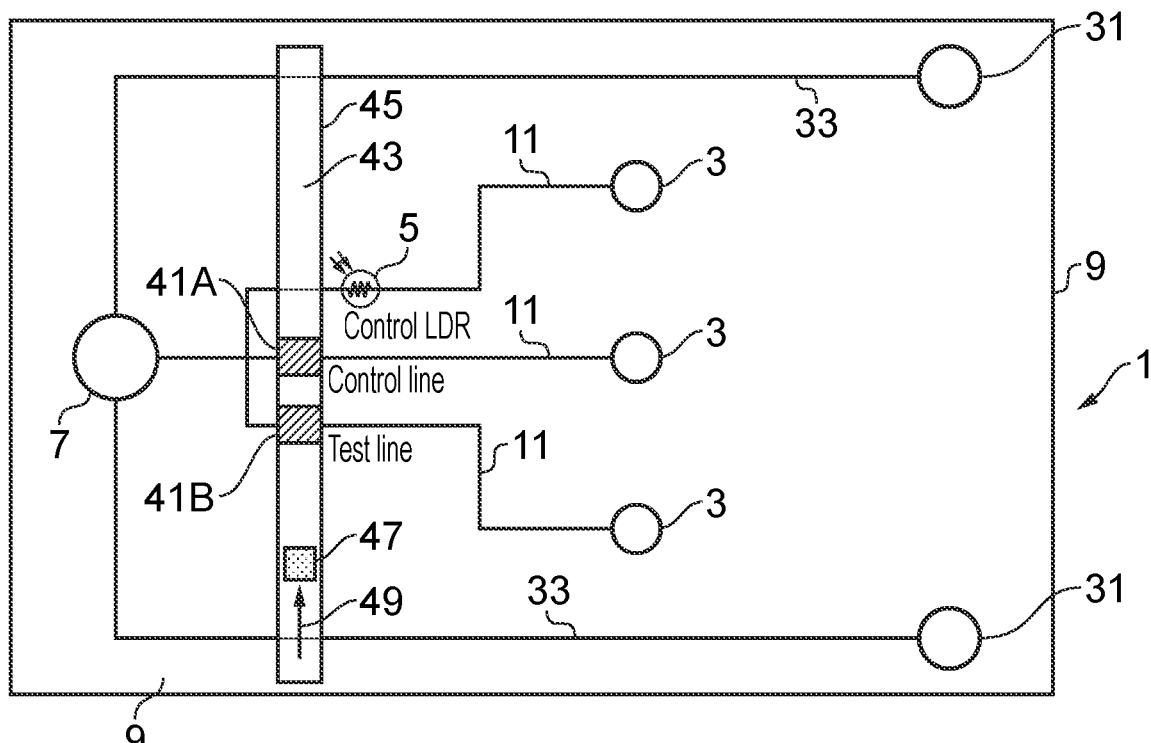
FIG. 4 illustrates an example apparatus and a test strip.

FIG. 4 illustrates the example apparatus 1 of FIG. 3 with integrated sensor elements 41. In the example of FIG. 4 the sensor elements 41 are provided within a lateral flow test 43. It is to be appreciated that any other types of test or sensors could be used in other examples of the disclosure.

The lateral flow test 43 comprises a test strip 45. The test strip 45 is a long, thin strip which is provided overlaying the substrate 9. A sample 47 may be added to the test strip 45. The sample 47 is then drawn along the test strip 45 by capillary action in the direction indicated by the arrow 49. The example test strip 45 of FIG. 4 comprises two sensor elements 41. The first sensor element 41A is a control line which is used to indicate whether or not the lateral flow test 43 has been successfully completed. The control line may change colour when the lateral flow test 43 has been completed.

The second sensor element 41B is a test line which is used to provide the test result. The second sensor element 41B indicates whether or not the analyte is present in the sample 47. The test line may change colour if the analyte is present.

The two sensor elements 41 are provided at different positions along the strip 45 so that each sensor element 41 overlays a different photo-resistive element 5. This enables different information electrodes 3 to be connected and disconnected from the ground electrode 7 by different sensor elements 41.

It is to be appreciated that other tests with different numbers and arrangement of sensor elements 41 may be used in other examples of the disclosure. Also in the example of FIG. 4 the sensor elements 41 change colour. It is to be appreciated that other changes in optical properties may be used in other examples of the disclosure.

When the lateral flow test 43 is provided overlaying the apparatus 1 the control line overlays a first photo-resistive element 5 and the test line overlays a second, different photo-resistive element 5. A third photo-resistive element 5 is not covered by the lateral flow test 43. The uncovered photo-resistive element 5 acts as a control photo-resistive element 5 and may be used to determine if the apparatus 1 is functioning correctly when the light of the capacitive touch screen is turned on and off.

In order to enable a capacitive touch screen to read the sensor elements 41 a user places the apparatus 1 on the surface of the touch screen and touches the ground electrode 7. In the example of FIG. 4 the lateral flow test 43 and the sensor elements 41 are initially transparent or at least partially transparent. This allows the light from the capacitive touch screen to be incident on the photo-resistive elements 5 which reduces the resistance of the photo-resistive element 5 and allows the respective information electrodes 3 to be connected to the ground electrode 7. This allows the information electrodes 3 to be detected by the capacitive touch screen.

If the test is completed then one or more of the sensor elements 41 change colour. This alters the illumination required to disconnect the information electrodes 3. For a given brightness of illumination this reduces the light incident on the respective photo-resistive elements 5 which increases the resistance. For a given brightness of illumination this may disconnect the respective information electrodes 3 from the ground electrode 7 so that the capacitive touch screen cannot detect the information electrode 3.

As the control photo-resistive element 5 is not covered by the lateral flow test the control photo-resistive element 5 always has light incident on it, provided the backlight is activated. This may be used to ensure that the apparatus 1 and capacitive touch screen are functioning correctly.

The reference electrodes 31 are always connected to the ground electrode and can be detected independently of the status of the backlight and the status of the lateral flow test and the sensor elements 41. The reference electrodes 31 may be used to enable the information electrodes 3 to be identified.

Table 1 indicates the electrode detection output for the apparatus of FIG. 4

| Test status | Test line output | Control line | Control photo-resistive element | Reference electrodes |
| --- | --- | --- | --- | --- |
| Ground electrode not touched | 0 | 0 | 0 | 0 |
| Ground electrode touched test not completed | 1 | 1 | 1 | 1 |
| Ground electrode touched test completed, positive result | 0 | 0 | 1 | 1 |
| Ground electrode touched test completed, negative result | 1 | 0 | 1 | 1 |

Therefore the example apparatus of FIG. 4 enables a capacitive touch screen to be used to read a lateral flow test 43 result.

In some examples the lateral flow test 43 may be integrated within the apparatus 1 so that the apparatus 1 and the lateral flow test 43 form a combined device. In other examples the lateral flow test 43 may be removably attached to the apparatus 1. This may enable the same apparatus 1 to be used to enable different lateral flow tests 43 to be read.

Figure 5:
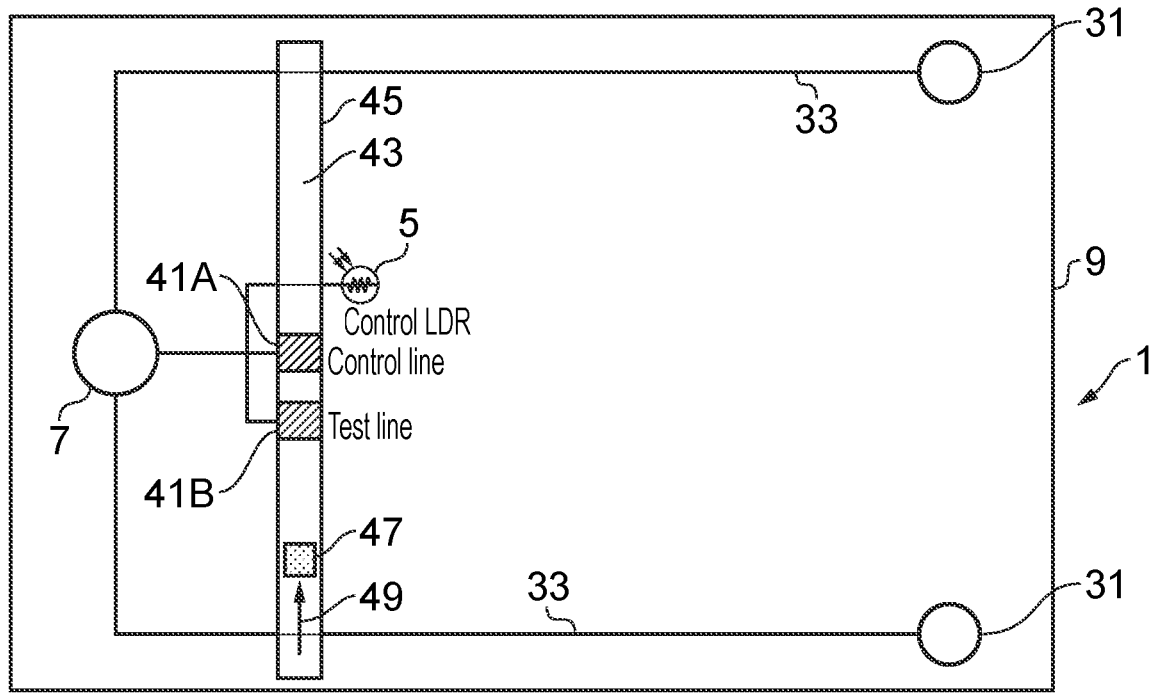
FIG. 5 illustrates an example apparatus in which the photo-resistive element forms part of the information electrodes.

FIG. 5 illustrates another example apparatus 1. The example apparatus of FIG. 5 is similar to the example apparatus of FIG. 4 except that in FIG. 5 the photo-resistive elements 5 form part of the information electrodes 3.

In the example apparatus 1 of FIG. 5 the photo-resistive elements 5 may comprise light dependent resistors which are large enough to act as an information electrode 3 as well as a switch. This may provide for a simplified apparatus 1 and may enable more electrodes 3 to be provided on the apparatus 1.

Figure 6:
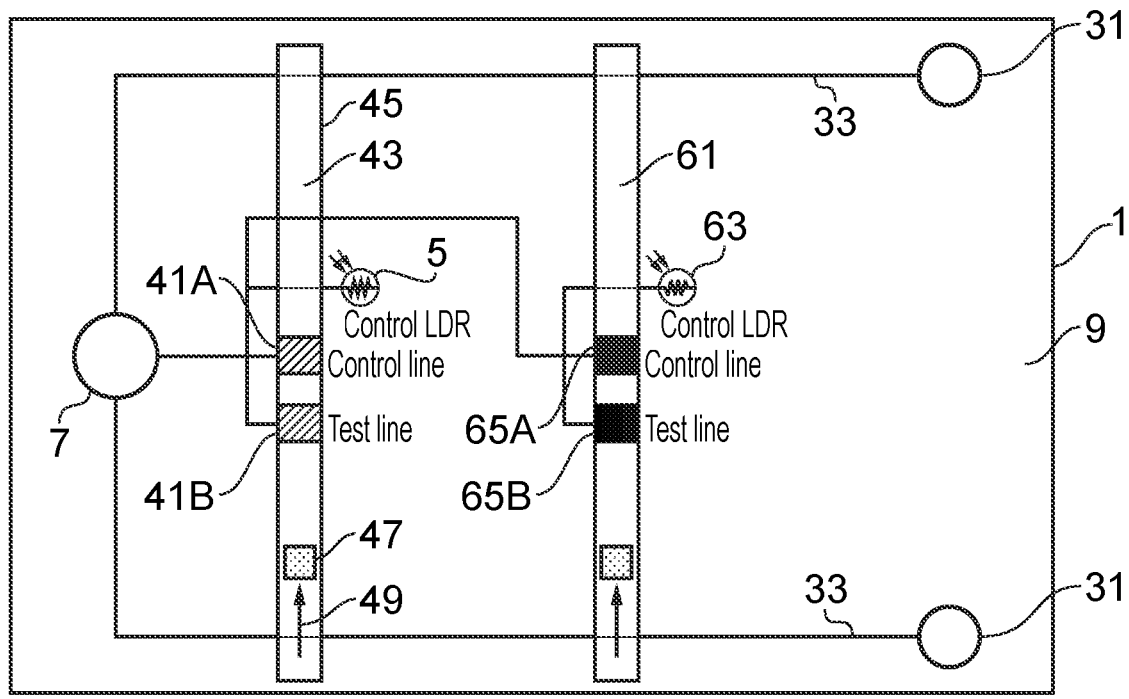
FIG. 6 illustrates an example apparatus comprising a calibration strip.

FIG. 6 illustrates another example apparatus 1. The example apparatus of FIG. 6 is similar to the example apparatus 1 of FIG. 5 except that in FIG. 6 the apparatus 1 comprises a calibration strip 61 in addition to the lateral flow test 43.

The example apparatus 1 of FIG. 6 comprises a plurality of information electrodes 3 which are used to enable information to be read from the lateral flow test 43. The apparatus 1 also comprises a plurality of calibration electrodes 63 which enable information to be read from the calibration strip 61. The calibration electrodes 63 may be identical to the information electrodes 3 so that they have the same size and shape and are connected to a ground electrode 7 by a photo-resistive element 5. In the example of FIG. 6 the photoresitive elements 5 form part of the calibration electrodes 63. It is to be appreciated that other arrangements may be used in other examples of the disclosure.

In the example of FIG. 6 three calibration electrodes 63 are provided however two of the calibration electrodes 63 are positioned underneath the calibration strip 61 and so are not illustrated in FIG. 6. The third calibration electrode 63 comprises a control calibration electrode 63 and is provided adjacent to the calibration strip. The control calibration electrode 63 may be used to ensure that the apparatus 1 is functioning correctly.

The calibration strip 61 may comprise one or more calibration elements 65. The calibration elements 65 may have optical properties which replicate a positive reading from the lateral flow test 43. The calibration strip 61 may ensure that correct readings are obtained regardless of the illumination properties and sensitivity of the capacitive touch screen.

In the example of FIG. 6 two calibration elements 65 are provided. The first calibration element 65A has optical properties which correspond to the optical properties of the control line when the lateral flow test 43 has been completed. The second calibration element 65B has optical properties which correspond to the optical properties of the test line when a positive result is obtained.

To read the lateral flow test 43 the brightness of the backlight at which the information electrodes 3 are no longer detected is determined. This may be compared to the brightness of the backlight at which the calibration electrodes 63 are no longer detected. This enables positive test results to be identified even if backlights have different intensities or if there is dirt or other material on the surface of the apparatus 1 or the capacitive touch screen. This may also enable the same apparatus 1 to be used with different touch screens which may have different sensitivities.

In some examples the calibration strip 61 may enable quantitative or semi-quantitative readings to be made. In such examples multiple calibration elements 65 may be provided corresponding to different concentrations of an analyte. By comparing the readings obtained from the information electrodes 3 with the readings from the calibration electrodes 63 the concentration of the analyte may be determined.

Figure 7:
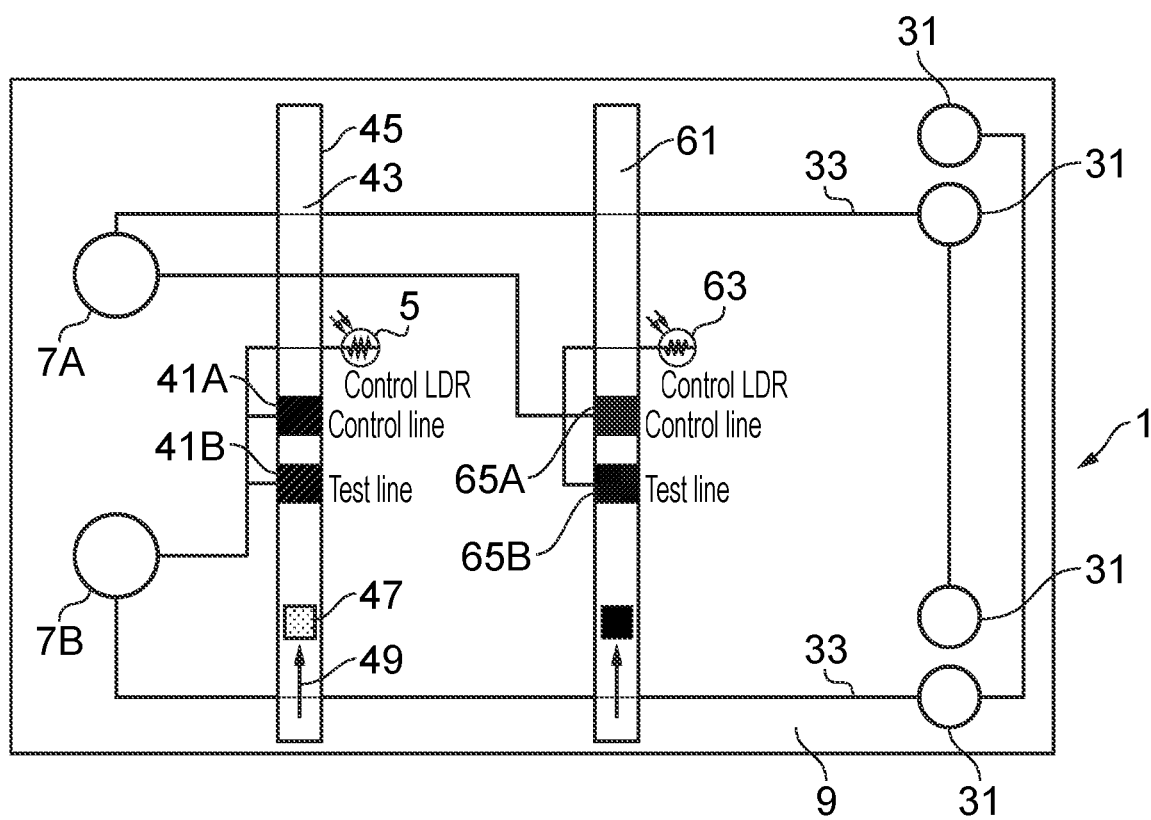
FIG. 7 illustrates an example apparatus comprising a plurality of ground electrodes.

FIG. 7 illustrates another example apparatus 1. The example apparatus of FIG. 7 is similar to the example apparatus 1 of FIG. 6 except that in FIG. 7 the apparatus 1 comprises a plurality of ground electrodes 7. In the particular example of FIG. 7 a first ground electrode 7A is provided for the calibration electrodes 63 and a second ground electrode 7B is provided for the information electrodes 3. Some of the information electrodes are underneath the test strip 45.

In the example of FIG. 7 the user may touch the different ground electrodes 7 at different times. This may enable the calibration electrodes 63 to be read at a different time to the information electrodes 3. This may be useful in examples where there are a plurality of different sensor elements 41 provided in a single test strip 45 and the capacitive touch screen is limited to the number of inputs that it can detect simultaneously.

In the example of FIG. 7 four reference electrodes 31 are provided. Each of the respective ground electrodes 7A, 7B is connected to different reference electrodes 31. This enables reference points to be provided when a user touches each of the different ground electrodes 7A, 7B.

In the above described examples only one lateral flow test 43 is provided on the apparatus 1. It is to be appreciated that in other examples a plurality of lateral flow tests 43 may be provided on a single apparatus 1. This may enable a plurality of lateral flow tests 43 to be read simultaneously or sequentially. The plurality of tests could be tests for different analytes within the same sample 47 or tests using different samples 47. The plurality of lateral flow tests 43 may also enable a quantitative analysis of the sample 47 as it may enable different threshold concentrations of the analyte to be detected. This may be achieved by having a plurality of different sensor elements 41 each with a different sensitivity to the same analyte.

In some examples the apparatus 1 may comprise a plurality of ground electrodes 7 so that each of the different lateral flow tests 43 may be coupled to information electrodes 3 which are connected to different ground electrodes 7. A user may enable each of the lateral flow tests 43 to be read sequentially by touching each of the ground electrodes 7 in turn.

Figure 8:
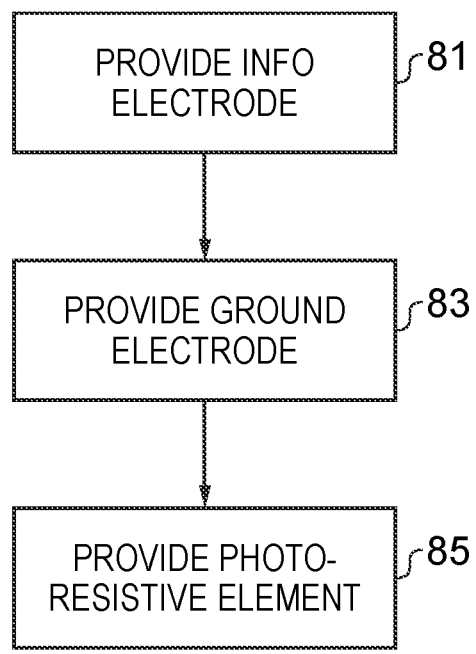
FIG. 8 illustrates a method.

FIG. 8 illustrates a method. The method may be used to provide example apparatus 1 as described above. The method comprises, at block 81, providing an information electrode 3 and, at block 83, providing a ground electrode 7. The method also comprises, at block 85, providing a photo-resistive element 5 configured to enable the information electrode 3 to be connected to the ground electrode 7. The photo-resistive element 5 is configured to enable a sensor element 41 to be positioned overlaying the photo-resistive element 5 such that a change in optical properties of the sensor element 41 controls the connection between the ground and information electrodes 7, 3.

FIGS. 9A to 9D illustrate another example method of forming an apparatus 1 such as the apparatus 1 described above. FIGS. 9A to 9D show the apparatus 1 at various stages of manufacture.

Figure 9A:
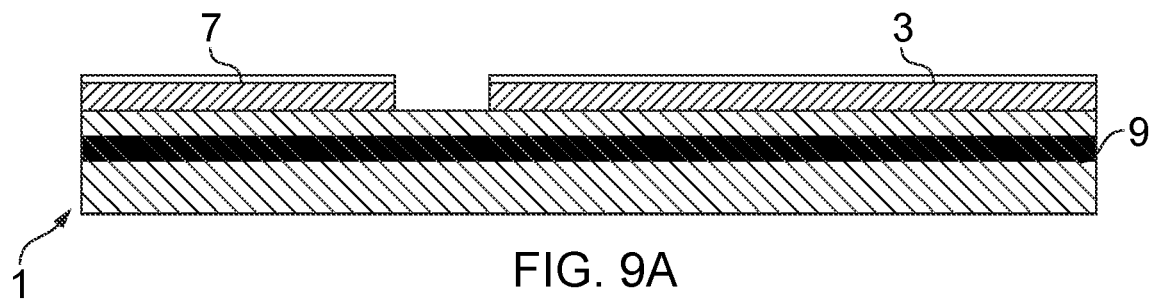
FIGS. 9A to 9D illustrate another example method.

In FIG. 9A conductive elements are patterned on a substrate 9. The conductive elements may comprise one or more ground electrodes 7 and one or more information electrodes 3 which may be as described above. In some examples other conductive elements such as reference electrodes 31, calibration electrodes 63 and any other suitable electrodes may also be patterned. The conductive elements may also comprise traces 11, 33 between the respective electrodes and the ground electrodes 7.

The conductive elements may be formed using any suitable means such as screen printing, inkjet printing, roll to roll printing, etching from an electrodeposited copper film or any other suitable technique.

The substrate 9 may be formed from any suitable material. The substrate 9 may be opaque so that external light does not activate the photo-resistive elements 5 when the apparatus 1 is in use. The substrate 9 may be made from paper, cardboard, PEN (polyethylene naphthalate), PET (polyethylene terephthalate), polyimide or any other suitable material.

Figure 9B:
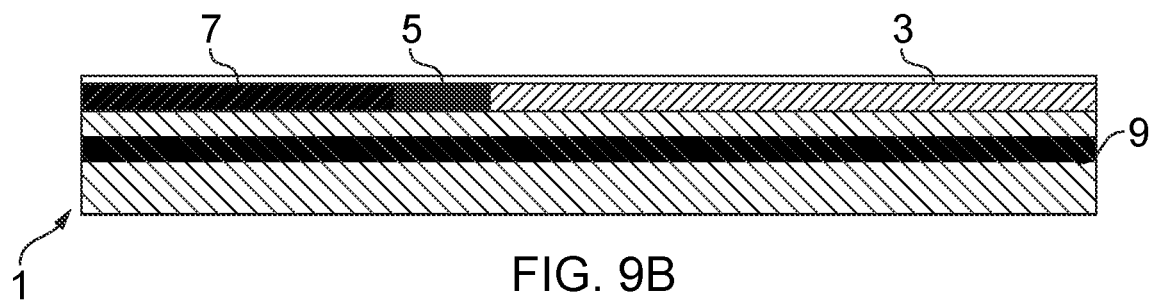

In FIG. 9B one or more photo-resistive elements 5 are formed. In some examples the photo-resistive elements 5 may be formed by printing a light dependent resistive material directly onto the electrodes 3, 7. An encapsulation layer may then be provided over the light dependent resistive material. In other examples a pre-fabricated photo-resistive element 5 may be bonded between the electrodes 3, 7.

Figure 9C:
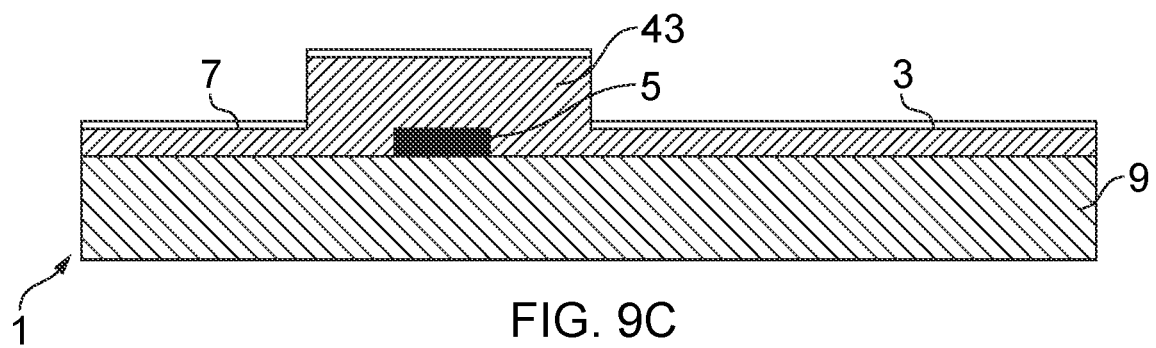

In FIG. 9C a lateral flow test 43 is integrated into the apparatus 1. The lateral flow test 43 is positioned on the apparatus 1 so that the sensor elements 41 overlay the photo-resistive elements 5. In the example of FIG. 9C the lateral low test 43 is laminated on top of the apparatus 1 with an adhesive.

In FIG. 9C only one lateral flow test 43 is illustrated. It is to be appreciated that any number of lateral flow tests 43 may be integrated into the apparatus 1. Also it is to be appreciated that the calibration strips 61 may be coupled to the apparatus in a similar manner to the lateral flow tests 43.

Figure 9D:
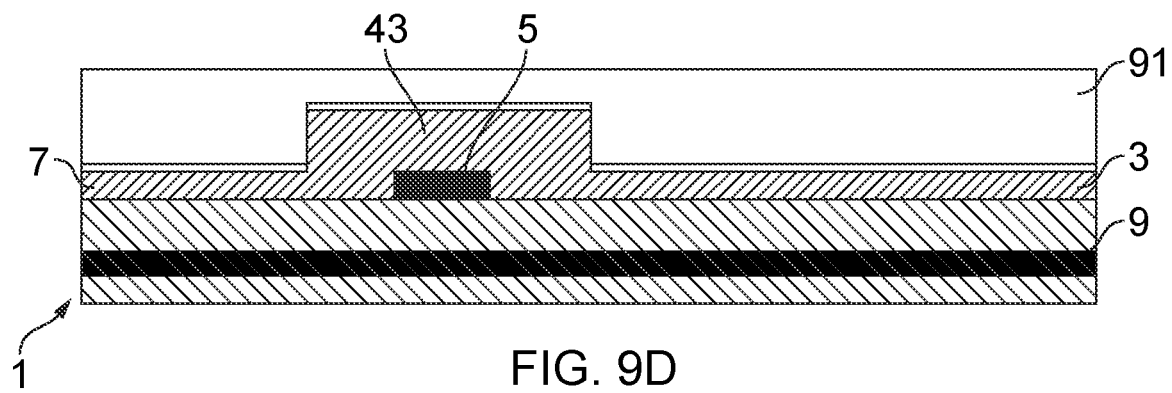

In FIG. 9D a cover material 91 is added to the apparatus 91. The cover material 91 may provide a passivation material which may increase the lifetime of the apparatus 1.

In some examples the cover layer may also be used to provide light adhesion to the surface of the capacitive touch screen. This may reduce light leakage between the surface of the apparatus 1 and the capacitive touch screen. It may also prevent the apparatus 1 from slipping on the surface of the capacitive touch screen. This may enable more accurate readings to be obtained over a period of time. This may be particularly beneficial in examples where the apparatus 1 comprises a plurality of ground electrodes 7 and different groups of information electrodes 3 are read at different times. The cover layer may be made from any suitable material such as polydimethylsiloxane (PDMS) or any other suitable material.

In some examples the cover material 91 may be opaque except for the regions over the photo-resistive elements 5. This may reduce light leakage and provide more accurate readings.

In the example of FIGS. 9C-9D the lateral flow test 43 is provided on the same side of the substrate 9 as the photo-resistive elements 5. The sensor element 41 may be provided adjacent to the photo-resistive elements 5. In other examples the lateral flow test 43 and sensor elements 41 may be provided on the opposite side of the substrate 9 to the photo-resistive elements 5. In such examples the substrate 9 is provided between the photo-resistive elements 5 and the sensor elements 41. In such examples the substrate 9 may be transparent to enable light to be transmitted from the sensor element 41 through the substrate 9.

Figure 10:
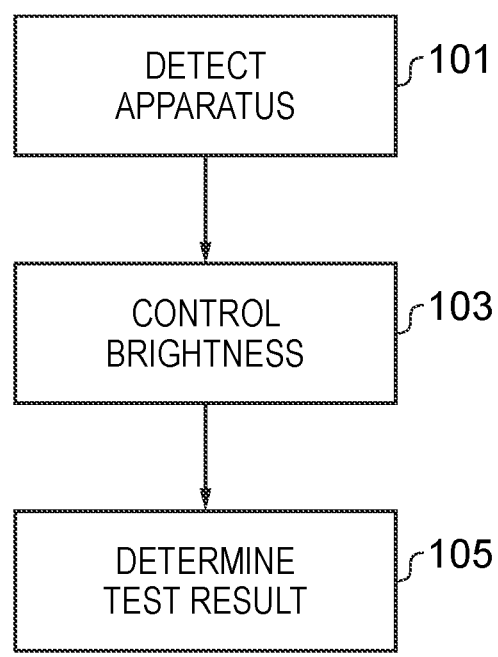
FIG. 10 illustrates a method of using an apparatus.

FIG. 10 illustrates an example method of reading information from an apparatus 1 such as the apparatus 1 described above. The method of FIG. 10 may be performed by an electronic device comprising a capacitive touch screen and light source.

At block 101 an apparatus 1 is detected on the capacitive touch screen. The apparatus 1 may be placed down. The electronic device may detect the apparatus 1 by detecting the reference electrodes 31.

The user may have to touch the ground electrode 7 in order for the reference electrodes 31 to be detected. In some examples the apparatus 1 may comprise more than one ground electrode 7. In such examples the electronic device may be configured to determine the location of the reference electrodes 31 and/or the ground electrode within the apparatus 1. This may enable identification of the electrodes 3, 63 which are being read.

At block 103 the brightness of the backlighting of the capacitive touch screen is controlled. The brightness may be gradually increased or decreased to determine the brightness at which the respective photo-resistive elements 5 are switched.

At block 105 the test result can be determined. The test result is determined by identifying which information electrodes 3 are connected and/or disconnected from the ground electrode 7. In some examples the test result may be determined by identifying the threshold brightness at which the photo-resistive element 5 is switched.

In some examples once the test result has been determined the electronic device may perform further actions on the test result. For example the test result could be stored in a database or information relating to the test result could be retrieved and provided to the user.

In examples where the apparatus 1 comprises a plurality of tests or samples 47, blocks 103 and 105 may be repeated as many times as necessary.

It is to be appreciated that variations of this method may be used in other implementations.

Figure 11:
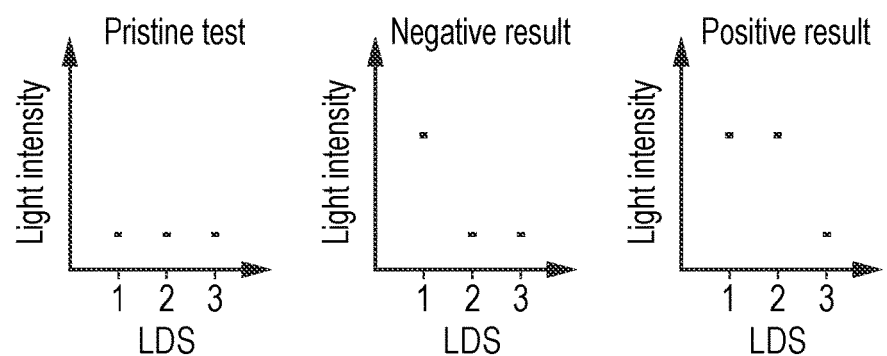
FIG. 11 illustrates results obtained with an example apparatus.

FIG. 11 illustrates example results obtained with an example apparatus 1. The results may be obtained using methods and apparatus 1 as described above.

In the example of FIG. 11 the 1 apparatus comprises three photo-resistive elements 5 and a single lateral flow test 43. The apparatus 1 could be the apparatus 1 of FIG. 4 or 5.

The first photo-resistive element 5A is configured to detect the state of the sensor element 41A comprising the control line. The second photo-resistive element 5B is configured to detect the state of the sensor element 41B comprising the test line. The third photo-resistive element 5C is a control photo-resistive element 5C and is arranged to provide a low threshold comparator.

In some examples performing a lateral flow alters the opacity or other optical components of the whole strip 45 due to the addition of fluid and salts and any other chemicals. In such examples the third photo-resistive element 5C may be positioned underneath the strip 45 to eliminate this variation.

FIG. 11 shows the arrangement of the respective photo-resistive elements 5 and the results of three test results. The test results are obtained by gradually increasing the intensity of the light provided by the capacitive touch screen.

In the pristine condition no sample 47 has been added to the lateral flow test 43. In this state all three photo-resistive elements 5 are switched at a low illumination threshold.

If a negative test is carried out this will change the optical properties of the control line but not of the test line. In this case the first photo-resistive element 5A is switched at a higher threshold than the other photo-resistive elements 5B, 5C.

If a positive test is been carried out this will change the optical properties of both the control line and the test line. In this case both the first photo-resistive element 5A and the second photo-resistive element 5B are switched at a higher threshold than the control photo-resistive element 5C.

Therefore the outcome of a test can be determined by comparing the respective photo-resistive elements 5. This may be achieved by gradually ramping the brightness of a touch screen and determining the threshold values for each photo-resistive element 5.

In some examples the optical properties of strip 45 may be uniform or only change slightly along the length of the strip before the lateral flow test 43 is used. This may ensure that the low threshold brightness is the same or similar for each of the photo-resistive elements 5. In other examples there may be significant differences in the optical properties at different positions along the strip 45. For instance the materials used as the sensor elements 41 may change the optical properties of the strip 45 even before the lateral flow test 43 us used. In such examples calibration elements 65 may be used for each position along the strip.

Figure 12:
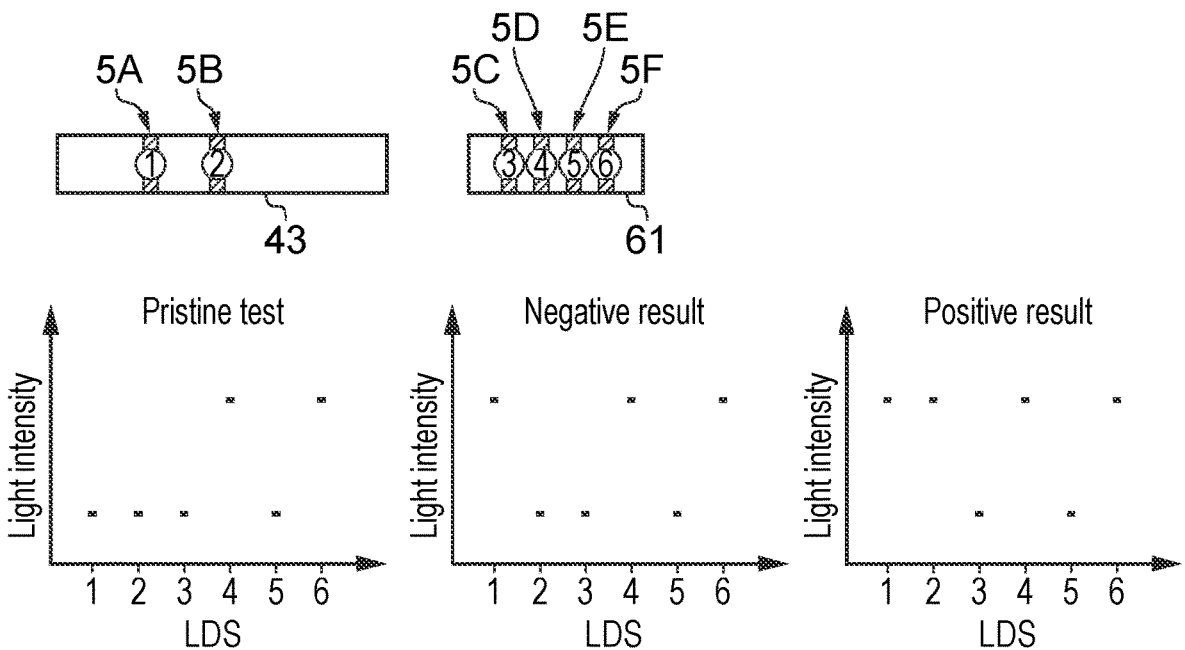
FIG. 12 illustrates results obtained with another example apparatus.

FIG. 12 illustrates results obtained with another example apparatus 1. The results may be obtained using methods and apparatus 1 as described above.

In the example of FIG. 12 the apparatus 1 comprises six photo-resistive elements 5, a single lateral flow test 43 and a calibration strip 61.

Two sensor elements 41 are provided on the lateral flow test 43. The first photo-resistive element 5A is configured to detect the state of the first sensor element 41A comprising the control line. The second photo-resistive element 5B is configured to detect the state of the second sensor element 41B comprising the test line.

The other photo-resistive elements 5C to 5F are configured to detect the state of the calibration elements 65 on the calibrations strip 61. The third photo-resistive element 5C provides calibration for a negative result from the test line and the fourth photo-resistive element 5D provides calibration for a positive result from the test line. The fifth photo-resistive element 5E provides calibration for a pristine control line and the sixth photo-resistive element 5F provides calibration for a positive result from the test line.

The example measurements of FIG. 12 are obtained by gradually increasing the brightness of the capacitive touch screen and noting the threshold of each photo-resistive element 5.

This may enable quantitative results to be obtained by including several positive result calibration elements 65 where each different positive result corresponds to the different levels of analyte. Direct comparison of the threshold of the test result with those of the positive result calibration samples 65 can then provide a quantitative result of level of analyte.

In the examples described above the photo-resistive elements 5 are triggered by the light from the capacitive touch screen. In some examples the photo-resistive elements 5 may be triggered by light of a particular wavelength or range of wavelengths. This may provide larger differences between thresholds and may enable more accurate results to be obtained.

In other examples each of the photo-resistive elements 5 may be the same but may be illuminated with light of a wavelength which is most strongly absorbed by the test strips. This may provide a large difference between a positive and negative result.

In some examples the electronic device may provide a flashing illumination for the apparatus 1. In such examples the electronic device may make use of the resistance recovery rate of the photo-resistive element 5 to measure a test result.

Figure 13A:
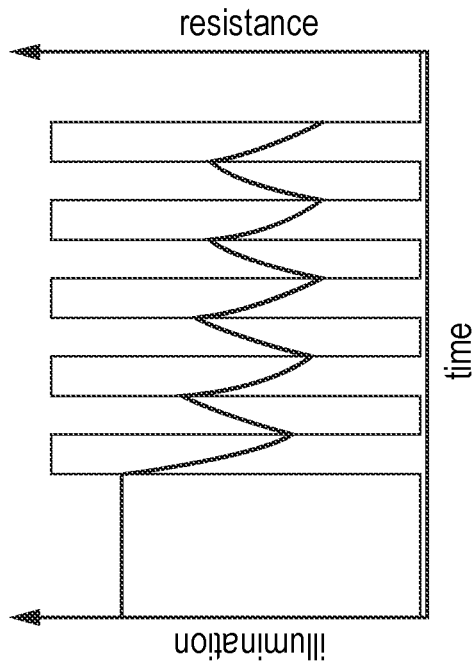
FIG. 13A to 13D illustrate example responses of photo-resistive elements.

FIG. 13A illustrates an example resistance response of a photo-resistive element 5. The photo-resistive element 5 may be an intrinsic resistor such as a CdS light dependent resistor. When light is incident on the intrinsic resistor the incident light excites electrons within the photo-resistive element 5 from the valence band to the conduction band. This increases the number of free electrons within the photo-resistive element 5 and reduces the resistance. The drop in the resistance will be proportional to the intensity of the incident light. The higher the intensity of the light the larger the drop in the resistance. Therefore the resistance of the photo-resistive element 5 is an inverse, non-linear function of the intensity of the incident light.

In materials such as CdS there is a time latency between changes in the incident light and the corresponding change in resistance. This latency is called the resistance recovery rate. The time taken for electrons to be excited to the conduction band and the resistance to drop after the photo-resistive element 5 has been illuminated is not the same as the time taken for electrons to drop to the valence band and the resistance to increase once the light has been removed. For instance, for a CdS light dependent resistor it typically takes about 1 s for the resistance to drop completely when light is applied after total darkness. However it can take up to 10 s for the resistance to rise back to the starting value after the complete removal of light. This property can be used in examples of the disclosure to read test results from example apparatus 1.

In examples of the disclosure, if the illumination source is switched on and off with a period lower than the resistance recovery rate of the photo-resistive element 5 then the resistance of the photo-resistive element 5 will be unable to reach the equilibrium value and will oscillate about an average value. If a light source flashes with a set ratio of time spent on and time spent off and only the frequency is changed the average resistance of the photo-resistive element 5 does not change and only the amplitude of the resistance oscillations is affected.

Figure 13B:
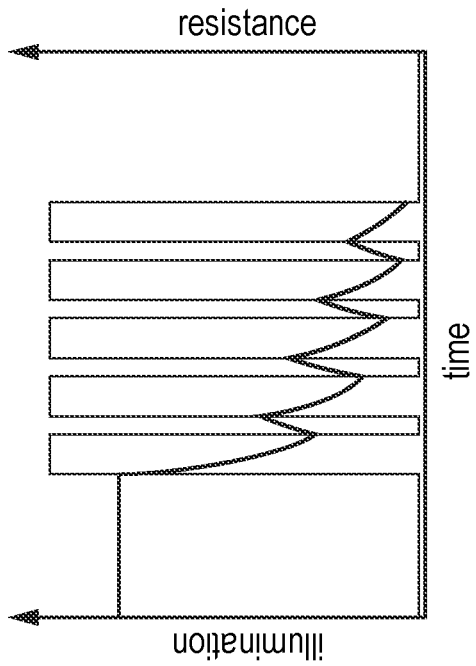
Figure 13C:
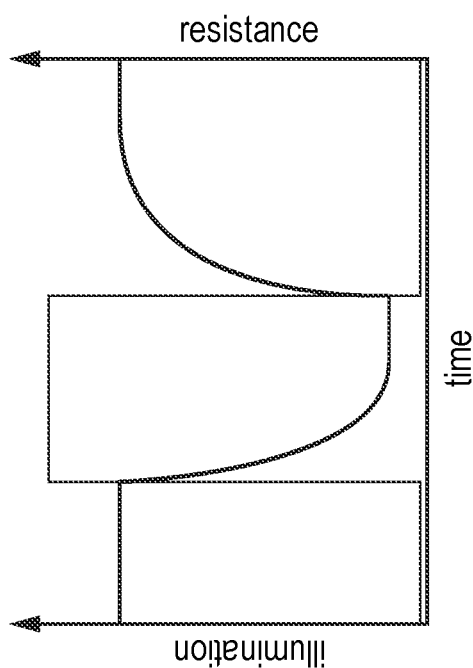
Figure 13D:
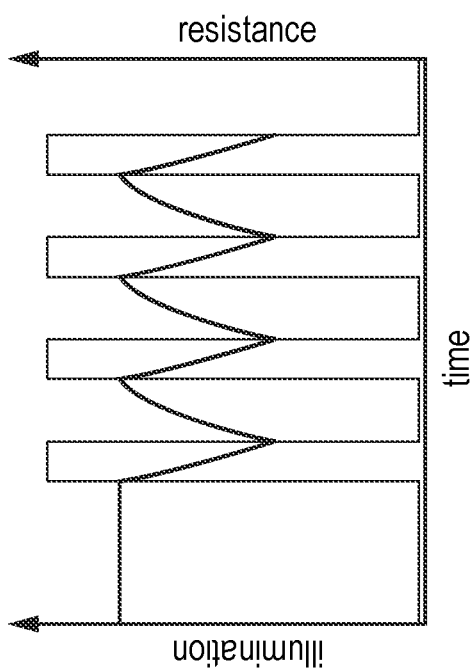

The average resistance of the photo-resistive element 5 can be controlled by varying the ratio of time spent with the illumination on and the time spent with the illumination off. FIGS. 13B to 13D show example resistance response of a photo-resistive element 5 with different ratios of time spent with the illumination on and the time spent with the illumination off. In the examples of FIGS. 13B to 13D the same time period is spent with the illumination on however the time spent with the illumination off is varied. The example of FIG. 13B has the largest time period with the illumination off and the example of FIG. 13D has the shortest time period with the illumination off. As the time period with the illumination off is decreased the photo-resistive element has less time to recover the resistance and so the resistance gradually decreases over time. A similar effect could be observed if the time period with the illumination off is kept constant but the time period with illumination on is varied. In some examples both the illumination on and illumination off time periods could be varied.

In examples of the disclosure varying the ratio of time spent with the illumination on and the time spent with the illumination off alters the average resistance of the light dependent resistor 5. In such examples the frequency of the light illuminating the apparatus 1 may be varied to change the average resistance of the photo-resistive element 5. By gradually varying the ratio of time with illumination on and time with illumination off a threshold frequency at which the average resistance disconnects the information electrode 3 may be determined.

The threshold frequency will be determined by the amount of light which is incident on the photo-resistive element 5. This will depend on the optical properties of the sensor elements 41 overlaying the photo-resistive element 5. Therefore a photo-resistive element 5 which is positioned under a positive sensor element 41 will have a different threshold frequency than a photo-resistive element 5 which is positioned under a negative sensor element 41. The threshold frequency could be compared to results obtained with calibration elements 65 to determine whether a positive or negative reading has been obtained.

This allows the test results of the apparatus 1 to be read by varying the frequency of the illumination rather than varying the brightness. This may be faster as there is no need to wait for the resistance to reach the equilibrium state. These examples can also be used with electronic devices which have limited brightness range, for example an e-reader or dedicated electronic device might have a single brightness value.

The apparatus 1 and methods described above provide the advantage that it enables sensor elements 41 to be read by capacitive touch screens.

This may enable sensor elements 41 which cannot be read manually to be used in example apparatus 1. For instance a user may be able to determine when a significant change in colour has been made but they might not be able to detect smaller changes in transparency fluorescence, gradual changes in colour or other optical properties. It may be possible to use examples of the disclosure to read test results that cannot be read accurately and/or reliably by a user.

Examples of the disclosure may also provide a simple way to enable a user to obtain contextual information about the test results. An electronic device may interpret the results of the test and provide the user with an interpretation of the results. In some examples the electronic device could be configured to compare the results of a plurality of tests. This could be a complex analysis which might not be possible for a user. The information could be in text format or other forms of media such as video or audio. This may enable the further information to be accessible to people who can't read.

In some examples the electronic device may enable information relating to the test result to be stored in a database. This may be useful where a large amount of data is created by the tests an apparatus 1. It also removes the need for the test result to be entered manually into a database and reduces the chance of errors being made. This information could have many uses. For instance it could allow results to be sent to a doctor or other remote health service provider. This could allow for remote testing and remove the need for medics to visit a patient. The data could be compiled from a large number of users which could be used to demonstrate disease or contamination spread over time.

Examples of the disclosure also enables the test result to be logged into a historical database to provide a historical record. This may be useful for farmers or people who have to take regular tests. The long term logging of results could also allow the historical data to be analysed and advice given based on multiple measurements. Data could also be shared remotely with other users. For instance information logged by a farmer could be available to a vet or information logged by a doctor or nurse could be provided to other health care providers.

In some examples the apparatus 1 may be a smart label which may be configured to be attached to goods or other objects. This may enable the environmental conditions of goods and other objects to which the apparatus 1 is attached be monitored. For example it may enable parameters such as humidity, temperature and the presence of chemicals or contaminants to be detected.

In the examples described above the term coupled means operationally coupled and any number or combination of intervening elements can exist (including no intervening elements).

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a features described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

For instance in some examples the apparatus 1 may also comprise one or more identification nodes. The identification modes may enable the sensor element and/or test result to be associated with a specific object.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus comprising:
   a substrate;
   an information electrode on the substrate;
   a ground electrode on the substrate;
   a conductive trace on the substrate, the conductive trace providing a path for direct current between the information electrode and the ground electrode;
   a photo-resistive element on the substrate, the photo-resistive element being on the path between the information electrode and the ground electrode; and
   a sensor element overlying the photo-resistive element, the sensor element having optical properties responsive to the presence of an analyte, such that a change in the optical properties of the sensor element occurring in response to the presence of the analyte controls the connection between the ground and information electrodes when light is passing through the sensor element to the photo-resistive element.

2. The apparatus as claimed in claim 1, wherein the photo-resistive element is positioned between the information electrode and the ground electrode.

3. The apparatus as claimed in claim 1, wherein the photo-resistive element forms part of the information electrode.

4. The apparatus as claimed in claim 1, further comprising a capacitive touch screen having a light source to illuminate the sensor element, wherein, when the substrate is placed on the capacitive touch screen, a connection of the information electrode to the ground electrode is detected.

5. The apparatus as claimed in claim 1, wherein the apparatus comprises a polymer coating.

6. The apparatus as claimed in claim 1, further comprising one or more additional information electrodes.

7. The apparatus as claimed in claim 1, further comprising one or more additional ground electrodes.

8. The apparatus as claimed in claim 1, further comprising at least one reference electrode.

9. The apparatus as claimed in claim 1, wherein the sensor element is integrated into the apparatus.

10. The apparatus as claimed in claim 1, wherein the sensor element comprises a material arranged to change optical properties in response to an analyte.

11. The apparatus as claimed in claim 1, wherein the sensor element is provided on an at least partially transparent test strip.

12. The apparatus as claimed in claim 1, further comprising a calibration strip.

13. The apparatus as claimed in claim 12, wherein the calibration strip enables the quantity of the analyte detected by the sensor element to be determined.

14. A test device comprising:
    a substrate;
    an information electrode on the substrate;
    a ground electrode on the substrate;
    a conductive trace on the substrate, the conductive trace providing a path for direct current between the information electrode and the ground electrode;
    a photo-resistive element on the substrate, the photo-resistive element being on the path between the information electrode and the ground electrode; and
    a sensor element overlying the photo-resistive element, the sensor element having optical properties responsive to the presence of an analyte, such that a change in the optical properties of the sensor element occurring in response to the presence of the analyte controls the connection between the ground and information electrodes when light is passing through the sensor element to the photo-resistive element.

15. A method comprising:
    providing a substrate;
    providing an information electrode on the substrate;
    providing a ground electrode on the substrate;
    providing a conductive trace on the substrate, the conductive trace providing a path for direct current between the information electrode and the ground electrode;
    providing a photo-resistive element on the substrate, the photo-resistive element being on the path between the information electrode and the ground electrode; and
    providing a sensor element overlying the photo-resistive element, the sensor element having optical properties responsive to the presence of an analyte, such that a change in the optical properties of the sensor element occurring in response to the presence of the analyte controls the connection between the ground and information electrodes when light is passing through the sensor element to the photo-resistive element.

* * * * *